United States Patent [19]
Reinhardt et al.

[11] Patent Number: 4,849,179
[45] Date of Patent: Jul. 18, 1989

[54] APPARATUS FOR TAKING SAMPLES BY THERMAL DESORPTION

[75] Inventors: Karl H. Reinhardt, Gülzow; Helmut Dittmer, Bleckede; Jürgen Gandress, Hamburg, all of Fed. Rep. of Germany

[73] Assignee: Kernforschungszentrum Karlsruhe GmbH, Karlsruhe, Fed. Rep. of Germany

[21] Appl. No.: 49,431

[22] Filed: May 14, 1987

[30] Foreign Application Priority Data

May 14, 1986 [DE] Fed. Rep. of Germany ....... 3616208

[51] Int. Cl.⁴ ............................................. G01N 30/06
[52] U.S. Cl. .......................................... 422/89; 55/67; 55/197; 55/386; 73/864.81; 73/864.91
[58] Field of Search ............................ 422/49, 88, 89; 436/161; 73/864.81, 864.91; 55/67, 197, 386

[56] References Cited
U.S. PATENT DOCUMENTS

| | | | |
|---|---|---|---|
| 2,357,638 | 9/1944 | Dwyer | 422/88 |
| 3,933,431 | 1/1976 | Trujillo et al. | 422/88 X |
| 4,003,257 | 1/1977 | Fletcher et al. | 422/89 X |
| 4,388,272 | 6/1983 | Gesteland | 422/88 X |
| 4,389,372 | 6/1983 | Lalin | 422/88 |
| 4,636,227 | 1/1987 | Yin et al. | 422/88 X |

Primary Examiner—Barry S. Richman
Assistant Examiner—Timothy M. McMahon
Attorney, Agent, or Firm—Spencer & Frank

[57] ABSTRACT

An apparatus for taking samples by thermal desorption of compounds that are adsorbed on solid adsorbents contained in a sample tube. An injector has a recess for accommodating the sample tube and a connection for a capillary column of a gas chromatograph. The compounds are desorbed into such capillary column by means of a stream of carrier gas passing through the sample tube. An injector extension is fastened to the injector and has a recess for accommodating the sample tube. The recess of the injector extension is flush with the recess of the injector. A push rod is guidable in the injector extension for pushing the sample tube from a position in the injector extension into a position within the injector. A carrier gas inlet communicates with the recess in the injector extension for admitting a carrier gas therein. A plug is disposed at an end of the push rod for gripping the sample tube. The plug includes a bore for effecting communication between the carrier gas inlet and the interior of the sample tube.

8 Claims, 2 Drawing Sheets

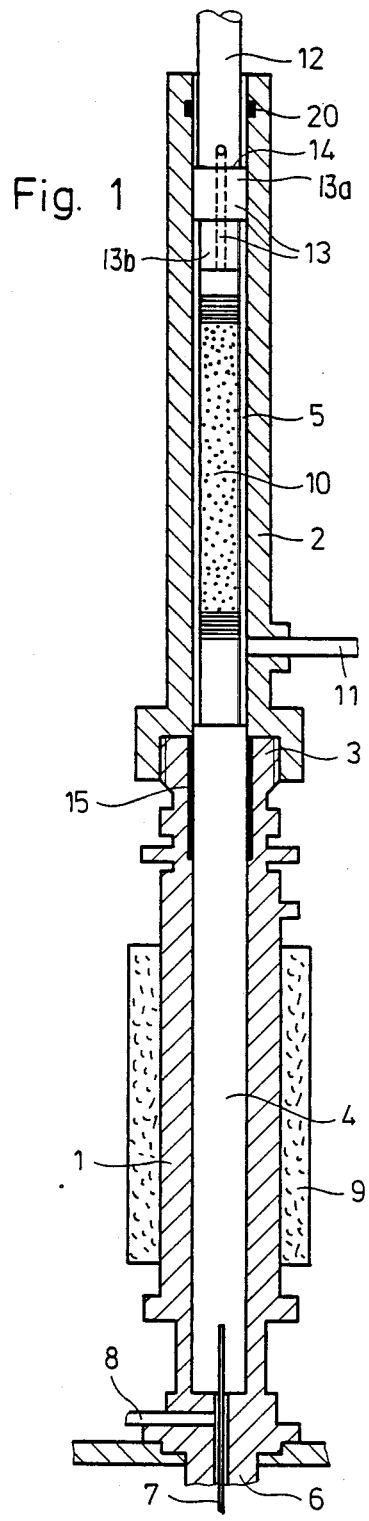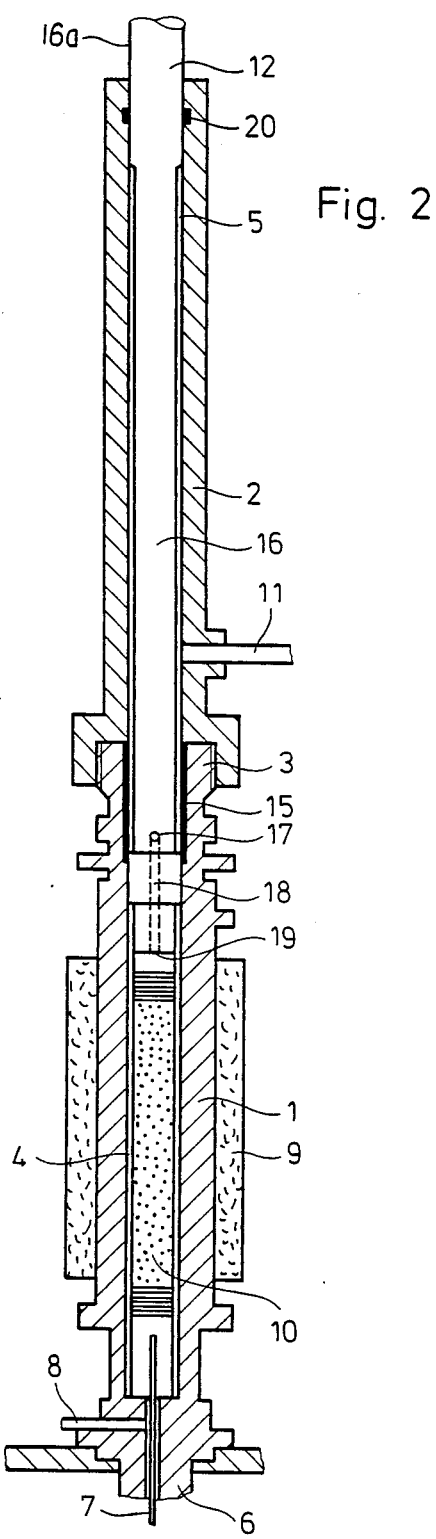

APPARATUS FOR TAKING SAMPLES BY THERMAL DESORPTION

BACKGROUND OF THE INVENTION

The present invention relates to an apparatus for taking samples by thermodesorption of components that are bound to solid absorbents, wherein (a) the absorbents are contained in a sample tube; and (b) the compounds are desorbed into a capillary column of a gas chromatograph by means of a stream of carrier gas and by way of an injector accommodating the sample tube.

The present invention relates particularly to an apparatus for injecting into the capillary column of a gas chromatograph trace substances which have been collected in sample tubes by adsorption from air or water.

Air and water are analyzed for their content of organic trace substances by pumping a stream of the medium to be examined over an adsorber pack on which the trace substances are collected and from which they are separated again by heating or elution with a solvent. The quantity of the trace substance, that is available for analysis however, is limited by the pump hold by the electrical power available for pumping. It is therefore desirable to inject the largest possible percentage of the collected trace substances into the capillary column of the gas chromatograph. Extracts cannot be evaporated to less than 100 $\mu$l if errors due to loss of the trace substance are to be avoided. However, injecting such small solvent quantities is very difficult. If liquid samples are injected into the capillary column of a gas chromatograph, one must therefore accept that only a small portion of the extracts, at most 10 $\mu$l, can be transferred to a capillary column, thus requiring large sample quantities.

The thermosdesorption technique has been developed to transfer the trace substances collected with the aid of a solid adsorbent into the capillary column of a gas chromatograph. All varieties of this technique have in common that the charged absorber tubes are inserted into a heated injection chamber through which flows a carrier gas and which is sealed off from the atmosphere so that the adsorbed substances can be transferred to a capillary without losses.

One prior art device is composed of a quartz sample tube having an enclosed cooling trap. The sample tube is filled with 200 mg TENAX resin from which the substances are desorbed by heating, whereupon they are frozen out in a subsequent quartz capillary by cooling with nitrogen. TENAX is a brand of porous material based on a polymer of 2,6-diphenyl-p-phenylene oxide. The desorbed components are thus concentrated into a narrow band. This desorption unit can also be used as a sample injection device for larger volumes of liquid samples which are collected with the aid of a small precolumn.

If wall influences do not matter, the precolumn may also be made of metal. Such a column, for example, has a length of 16 cm and is made of $\frac{1}{8}$" high-grade steel filled with TENAX GC 60/80 mesh. It is connected in an electric circuit as a resistor to effect resistive heating or is heated by means of a portable furnace.

If the substances are quickly released by heating, freezing may be omitted. For example, a commercially available device, operating with microwave heating, causes trace substances that are adsorbed by activated carbon, for example various ethers or Diesel fuel, to be desorbed. However, this method is limited to adsorption agents which can be heated by microwaves. Many polymers are not heated enough by such a device. For example, the adsorption agent TENAX, which is particularly suitable for collecting less volatile compounds, cannot be heated sufficiently with this device.

Many prior art injection devices contain heated valves, desorption furnaces or heated conduits. With the simpler devices, in which the adsorption sample tube is inserted into the injector, sample losses must be expected due to incomplete desorption of less volatile compounds.

Although, due to its thermal stability. TENAX is also suitable for desorption at higher temperatures, the task of transferring compounds having a higher boiling point to the capillary column by heating is accomplished only incompletely by the prior art devices.

Tests made with a commercially available thermodesorption device show that less volatile substances such as hexachlorobenzene and polychlorinated biphenyls can be transferred to the capillary column of the gas chromatograph only with considerable losses even if the carrier gas split connection is closed.

SUMMARY OF THE INVENTION

It is an ojbect of the present invention to improve the above-mentioned device so that charged adsorber tubes can be inserted into an injector in a particularly simple manner and the complete transfer of the sample substances becomes possible while avoiding stress on the adsorber and on the capillary column due to atmospheric air.

The above and other objects are accomplished according to the invention in the context of an apparatus for taking samples by thermodesorption of compounds that are bound to solid adsorbents, wherein the apparatus includes a sample tube containing solid adsorbents, and an injector having a recess for accommodating the sample tube and having a connection for a capillary column of a gas chromatography, the compounds being desorbed into such capillary column by means of a stream of carrier gas passing through the sample tube. According to the invention the apparatus additionally includes:

an injector extension fastened to the injector and having a recess for accommodating the sample tube, the recess of the injector extension being flush with the recess of the injector;

a push rod guidable in the injector extension for pushing the sample tube from a position in the injector extension into a position within the injector;

carrier gas inlet means communicating with the recess in the injector extension for admitting a carrier gas therein; and a plug disposed at an end of the push rod adjacent to the sample tube for gripping the sample tube, the plug including a bore for effecting communication bettween the carrier gas inlet means and the interior of the sample tube.

With the aid of simple injector extension fastened to the injector by a threaded coupling, it is thus accomplished that the sample tube, while being heated in the injector, is not only in contact with the carrier gas but the carrier gas also flows through it will a constant flow so that all substances are directly desorbed to the capillary. The threaded coupling is suitable in principle for all injectors with splitless injection mode. The injector extension may be fastened to the injectors of various manufacturers by means of suitable adapters. It is of particular advantage for the charged sample tube to be inserted, without the actuation of valves, into the injector through which the carrier gas flows and to be heated within the stream of carrier gas so that the adsorbed substances are directly desorbed into the capillary column. This eliminates errors due to impurities in the laboratory air. With this type of sample injection it is also possible to inject larger quantities of liquid samples. Thus, there is no longer any need to condense the extracts.

BRIEF DESCRIPTION OF THE DRAWINGS

The invention will be described in greater detail below with reference to an embodiment which is illustrated in the accompanying drawings, wherein:

FIG. 1 is a longitudinal cross section of a thermodesorption device according to the invention with a charged sample tube disposed in the injector extension;

FIG. 2 is a similar view of the device of FIG. 1, with the charged sample tube disposed in the injector.

DESCRIPTION OF THE PREFERRED EMBODIMENTS

Figure 3:
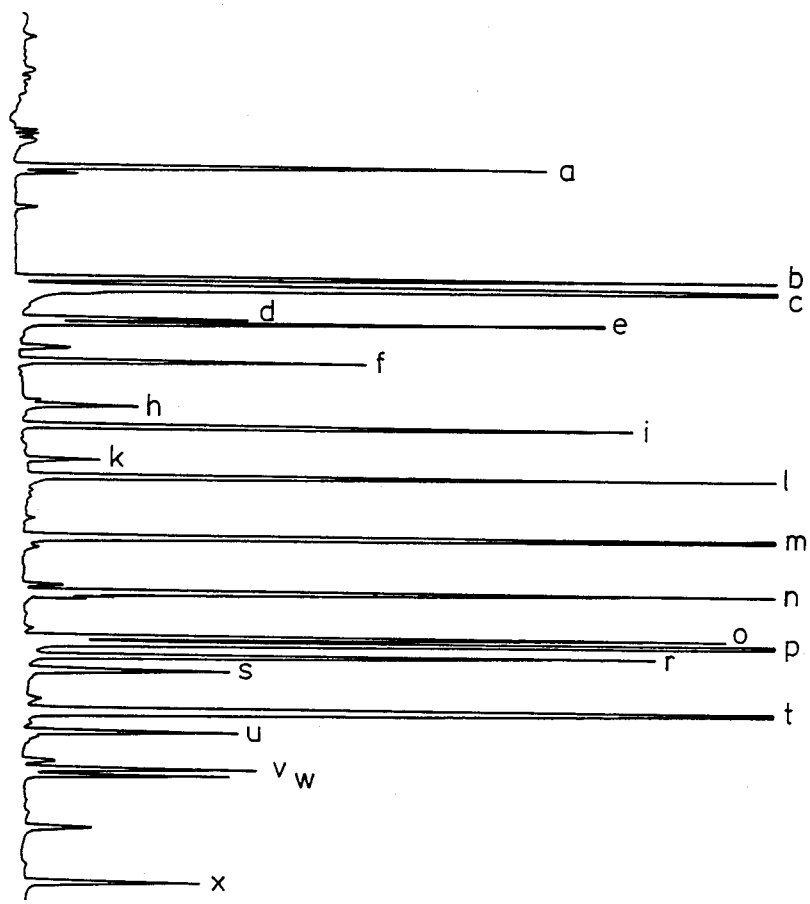
FIG. 3 is a chromatogram of a trace substance desorbed by a desorption device according to the invention.

FIGS. 1 and 2 are sectional views of an injector extension 2 coupled to an injector 1. Both parts 1 and 2 have basically an elongated cylindrical shape and can be screwed to one another at adjoining ends, with a threaded coupling 3 being provided for this purpose. Each one of parts 1 and 2 is provided with a recess 4 and 5, respectively, both having the same cross section and being flush with one another. At its lower frontal face 6, injector 1 has a connection for a capillary column 7 and a split connection 8 for the discharge of a carrier gas. A heating device 9 with which the thermodesorption from a sample tube 10 filled with solid adsorbents is effected is arranged around injector 1. In the region of threaded coupling 3, injector extension 2 is connected on its side to a carrier gas intake 11 which is in communication with recesses 4 and 5.

The charged sample tube 10 is initially introduced into injector extension 2 by means of a push rod 12. A plug 13, for example of plastic, such as TEFLON, is provided for this purpose and is composed of a first portion 13a fastened to the frontal face 14 of push rod 12 and a second, smaller diameter, portion 13b inserted with a tight fit into the upper opening of sample tube 10. In this position, which is shown in FIG. 1, recesses 4 and 5 may be in communication with one another and may be rinsed, along with the exterior of sample tube 10, with a carrier gas admitted via gas intake 11.

In the injection position shown in FIG. 2, the frontal face of charged sample tube 10 is placed snuggly onto the connection of capillary column 7. To do this, sample tube 10 is transferred into recess 4 by means of push rod 12. To improve guidance and the seal against gas conduits, which are not required in this operating mode of the injector, recess 4 may be provided with a sleeve 15 in the region of threaded coupling 3, with such sleeve being adapted in a sealing manner to the outer larger diameter portion 13a of plug 13.

Following plug 13, push rod 12 has a tapered region 16 of a length which is sufficient so that, in the injection position (FIG. 2) carrier gas can flow through intake 11 and along the outside of push rod 12 toward an opening 17 in the outer jacket or surface of push rod 12. Opening 17 provides access to a bore 18 extending through push rod 12 and plug 13 to the frontal face 19 of plug 13 so that a through connection is formed for the carrier gas from inlet 11 to the head end of charged sample tube 10.

On the other hand, the length of tapered region 16 is made short enough that a reinforced region 16a of push rod 12 in the injection position of FIG. 2 is surrounded by a seal in the form of a gasket 20. Gasket 20 is embedded in the wall of interior extension 2 and prevents the escape of carrier gas to the environment and forces it through charged sample tube 10.

The quartz or glass sample tube 10, filled with TENAX and charged with the substances to be examined, has precisely the dimensions of an injector insert normally employed for sample injection with or without splitting the carries gas stream and is inserted into the heated portion of injector 1 by means of push rod 12 the plug 13 and is heated from 5 to 20 minutes at 250° C., while the capillary column is at room temperature. Push rod 12, when the the lowered position (FIG. 2), is preferably sealed against the atmosphere by means of gasket 20. When push rod 12 is raised as shown in FIG. 1, carrier gas escapes at the top of injector extension 2.

In the injector position of FIG. 2, carrier gas enters into the annular chamber between push rod 12 and injector extension 2 and is conducted through opening 17 and bore 18 to frontal face 19 to the adsorber fill of sample tube 10. Plug 13 on which tube 10 is seated, prevents the carrier gas from flowing past tube 10 on the exterior and thus forces the elution of the less volatile components. These are collected by capillary column 7 which is kept at room temperature. For hexachlorobenzene and higher boiling point substances, experience has shown that no additional cooling is necessary, it being found, surprisingly, that the peaks of the higher boiling point substances become sharp nevertheless.

FIG. 3 is the chromatogram of a standard solution of less volatile organochlorine compounds, 2 $\mu$l of which were injected into a TENAX filled sample tube 10 so that the quantities of each individual substance wele between 20 and 70 pg. Charged sample tube 10 was heated in injector 1 for 20 minutes at 250° C. with split connection 8 closed. During this time, capillary column 7 was at room temperature. The chromatogram of FIG. 3 shows sharp peaks which area approximately comparable to those obtained with on-column injection.

It will be understood that the above description of the present invention is susceptible to various modifications, changes and adaptations, and the same are intended to be comprehended within the meaning and range of equivalents of the appended claims.

We claim:

1. An apparatus for taking samples by thermal desorption of compounds that are adsorbed on solid adsorbents, the apparatus including:
   a sample tube containing solid adsorbents; and
   an injector having a recess for accommodating the sample tube and having a connection for a capillary column of a gas chromatograph, compounds being desorbed into such capillary column by means of a stream of carrier gas passing through the sample tube; the improvement comprising:
   an injector extension fastened to said injector and having a recess for accommodating the sample tube, the recess of said injector extension being flush with the recess of said injector;

a push rod guidable in said injector extension for pushing said sample tube from a first position in said injector extension into a second position within said injector;

carrier gas inlet means communicating with the recess in said injector extension for admitting a carrier gas therein; and a plug disposed at an end of said push rod adjacent to said sample tube for gripping said sample tube, said plug including a bore for effecting communication between said carrier gas inlet means and the interior of said sample tube when said push rod has moved said sample tube into said injector recess.

2. Apparatus as defined in claim 1, wherein said push rod has a tapered region having an outer surface adjacent said plug; said plug has a frontal face facing the interior of said sample tube; and said bore extends from the frontal face of said plug to said outer surface of said push rod in said tapered region.

3. Apparatus as defined in claim 1, wherein said injector extension has a free frontal face and further including means for sealing the recess in said injector extension against said push rod and the environment near said free frontal face.

4. Apparatus as defined in claim 1, including means defining a threaded coupling for joining said injector extension with said injector.

5. Apparatus as defined in claim 1, wherein said carrier gas inlet means is disposed at a side of said injector extension.

6. Apparatus as defined in claim 1, including a guide sleeve fitted in the recess of said injector at the end of said injector adjacent said injector extension for guiding said plug in a sealing manner.

7. Apparatus as defined in claim 1, wherein said sample tube has a frontal face with means defining an opening, and said plug is inserted into said opening.

8. Apparatus as defined in claim 1, including means for insing recesses and said sample tube with a carrier gas when said sample tube is in said second position.

* * * * *

UNITED STATES PATENT AND TRADEMARK OFFICE
CERTIFICATE OF CORRECTION

PATENT NO. : 4,849,179
DATED     : July 18, 1989
INVENTOR(S) : Karl H. Reinhardt et al.

It is certified that error appears in the above-identified patent and that said Letters Patent is hereby corrected as shown below:

On the title page:

In the heading of the inventors under [75], the third inventor's last name should read -- Gandrass -- .

Signed and Sealed this

Eighth Day of January, 1991

Attest:

HARRY F. MANBECK, JR.

*Attesting Officer*  *Commissioner of Patents and Trademarks*